(12) United States Patent
Creedon et al.

(10) Patent No.: US 10,039,631 B2
(45) Date of Patent: Aug. 7, 2018

(54) IMPLANT DEVICE FOR USE IN SALIVARY GLAND DUCT

(71) Applicant: E. Benson Hood Laboratories, Pembroke, MA (US)

(72) Inventors: Dennis F. Creedon, Sandwich, MA (US); Lewis H Marten, Westwood, MA (US)

(73) Assignee: E. BENSON HOOD LABORATORIES, Pembroke, MA (US)

( * ) Notice: Subject to any disclaimer, the term of this patent is extended or adjusted under 35 U.S.C. 154(b) by 79 days.

(21) Appl. No.: 14/828,769

(22) Filed: Aug. 18, 2015

(65) Prior Publication Data
US 2016/0045301 A1     Feb. 18, 2016

Related U.S. Application Data

(60) Provisional application No. 62/038,650, filed on Aug. 18, 2014.

(51) Int. Cl.
*A61F 2/04*     (2013.01)
*A61B 17/24*    (2006.01)

(52) U.S. Cl.
CPC .............. *A61F 2/04* (2013.01); *A61B 17/24* (2013.01); *A61F 2220/0008* (2013.01); *A61F 2230/0069* (2013.01); *A61F 2250/0039* (2013.01); *A61F 2250/0059* (2013.01)

(58) Field of Classification Search
CPC ................................. A61F 2/04; A61B 17/24
See application file for complete search history.

(56) References Cited

U.S. PATENT DOCUMENTS

| | | | | |
|---|---|---|---|---|
| 6,017,355 | A  * | 1/2000 | Hessel ..................... | A61F 5/445 604/174 |
| 2012/0010555 | A1* | 1/2012 | Creedon ................... | A61F 2/04 604/8 |
| 2014/0379005 | A1* | 12/2014 | Trabucco .............. | A61F 2/0063 606/151 |
| 2016/0135941 | A1* | 5/2016 | Binmoeller ............... | A61F 2/04 623/23.7 |

* cited by examiner

*Primary Examiner* — Thomas J Sweet
*Assistant Examiner* — Daniel Bissing
(74) *Attorney, Agent, or Firm* — Wissing Miller LLP

(57) ABSTRACT

An implant device having a proximal end and a distal end, and a suturing fixture offset from the proximal end. The suturing fixture has a profile that extends from the surface of the elongate body. For example, the suturing fixture may have the shape of a cone, or the shape of a disc. The implant device may be used for placement within a salivary gland duct.

20 Claims, 12 Drawing Sheets

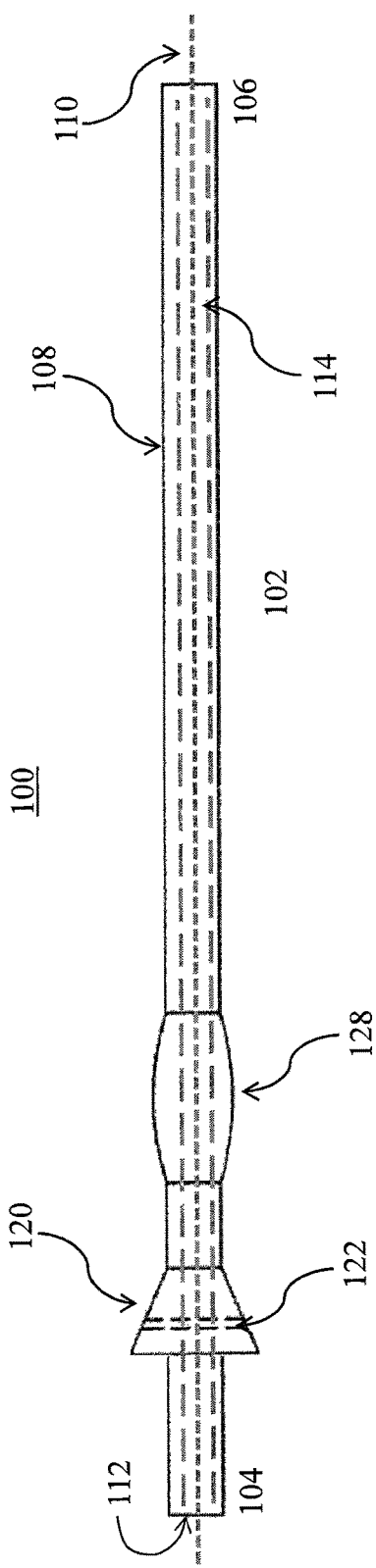
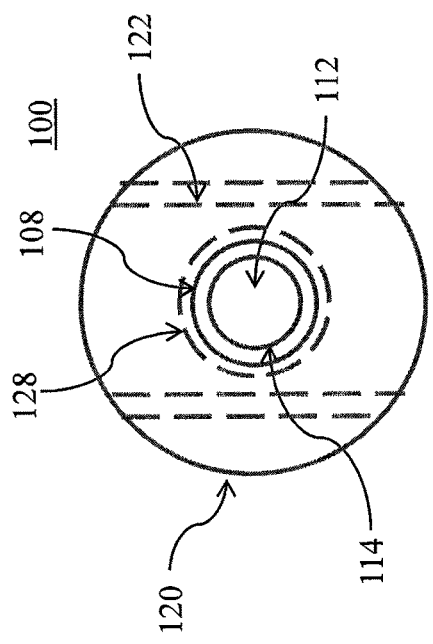
FIG. 2A
FIG. 2B

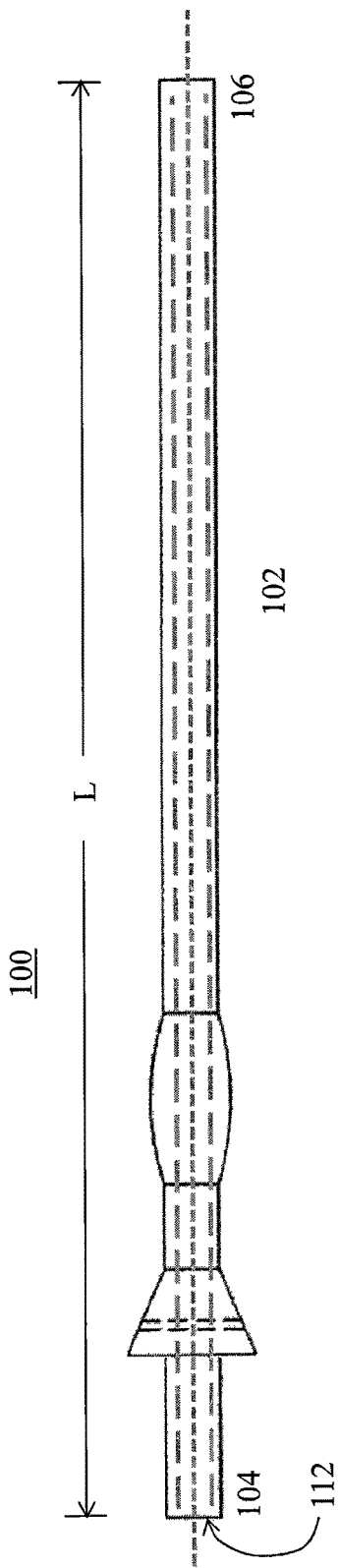
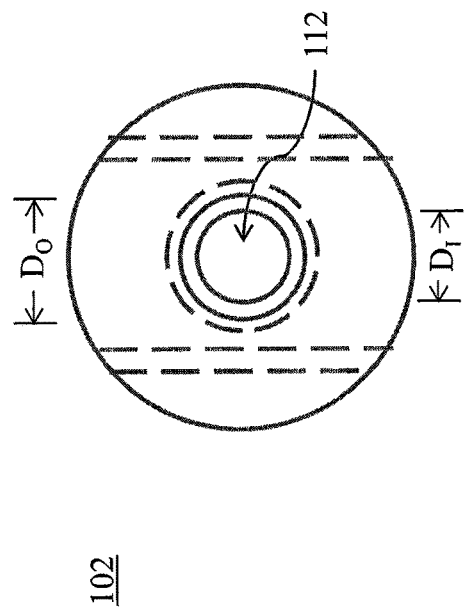
FIG. 3A
FIG. 3B

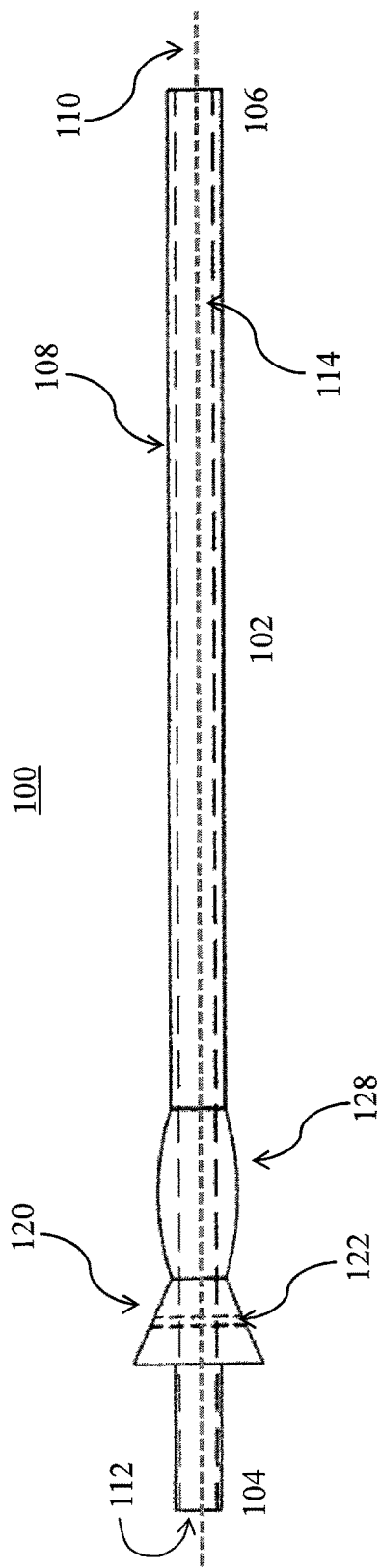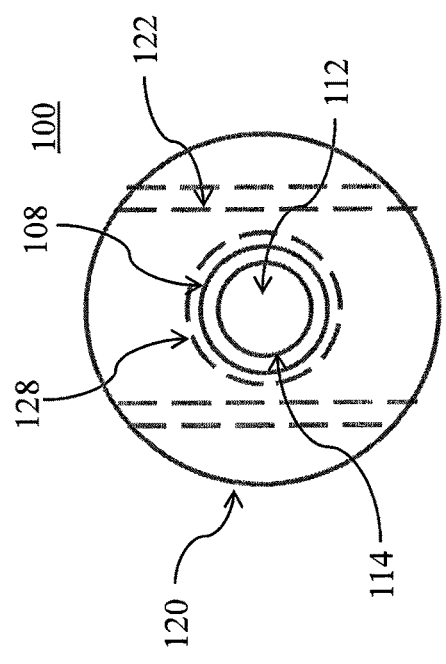
FIG. 12A
FIG. 12B

IMPLANT DEVICE FOR USE IN SALIVARY GLAND DUCT

CROSS REFERENCE TO RELATED APPLICATIONS

This application claims priority to U.S. provisional application Ser. No. 62/038,650 filed on Aug. 18, 2014, which is incorporated herein by reference.

FIELD OF THE INVENTION

The instant invention is directed to a medical implant device. More particularly, the instant invention is directed to a medical implant device used in the treatment of salivary duct channels.

BACKGROUND OF THE INVENTION

Salivary glands are found in and around a person's mouth and throat. The major salivary glands are the parotid, submandibular, and sublingual glands. These glands provide the needed saliva to assist in food chewing and early digestion of certain carbohydrates, and they support the sense of taste. Saliva is drained through salivary ducts into the oral cavity: the parotid duct connects from the parotid gland to near the upper teeth, the submandibular duct connects from the submandibular gland to under the tongue, and the duct of Rivinus connects from the sublingual gland to the floor of the mouth on the sublingual fold.

Among the different salivary gland problems encountered, obstruction of the flow of saliva via the salivary gland ducts may be the most common. This may be caused by the formation of stones, which can become lodged in the duct and prevent the saliva produced in the salivary gland from exiting the ductal system and entering the oral cavity. The lack of saliva flow contributes to dry mouth disorder and can cause swelling of the salivary gland, leading to pain and possible infection.

Other problems may include the development of kinks in the salivary gland ducts, stenosis (i.e., constriction or narrowing) of the salivary gland ducts, or generally other structural or structurally-related defects associated with the salivary glands and/or salivary gland ducts.

It is therefore advantageous to facilitate the integrity of the salivary ducts and their respective glands, especially when their integrity is compromised, and to treat the glands rather than remove them.

SUMMARY OF THE INVENTION

It is an object of the invention to provide a salivary gland implant device that is operable, among other functions, to maintain, repair, and/or restore the structure and functionality of salivary gland ducts, and that is simple to remove once this is accomplished.

An aspect of the invention relates to a salivary gland implant device for placement within a salivary gland duct. The device may comprise an elongate body having a proximal end and a distal end, and a suturing fixture offset from the proximal end. The elongate body may comprise an axis that extends through the middle of the elongate body between the proximal end and the distal end. In some embodiments, the elongate body may be generally cylindrical in shape. In certain embodiments, the elongate body comprises a lumen that extends through the body, for example, parallel to the axis.

The suturing fixture may comprise a profile that extends radially outward from the elongate body. In certain embodiments, the suturing fixture may comprise a cone, such as a truncated cone, or it may comprise a disc. In some embodiments, the suturing fixture may comprise one or more suture channels.

In certain embodiments, the implant device may further comprise a bulb that is distal to the suturing fixture. The bulb may comprise a radius that is greater than the radius of the elongate body.

Another aspect of the invention relates to a scope that may be used with the implant device. The scope may comprise a small diameter and is flexible.

A further aspect of the invention relates to a salivary gland implant device kit comprising the salivary gland implant device. The kit may further comprise a wire guide, a scope, a balloon catheter, and/or a duct dilator.

An additional aspect of the invention relates to a method for implanting the salivary gland implant device within a salivary gland duct. The method comprises suturing the suturing fixture of the implant device to a location adjacent to the parotid gland. Upon placement of the implant device within the salivary gland duct, saliva flows postoperatively in the salivary duct along the implant device's outer surface, or in some embodiments, through the lumen of the implant device.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which:

FIGS. 2A and 2B illustrate a cut-away side view perspective (FIG. 2A) and an end view perspective (FIG. 2B) of a salivary gland duct implant device according to embodiments of the present invention;

FIGS. 3A and 3B illustrate a cut-away side view perspective (FIG. 3A) and an end view perspective (FIG. 3B) of a salivary gland duct implant device according to embodiments of the present invention;

FIGS. 12A and 12B illustrate a cut-away side view perspective (FIG. 12A) and an end view perspective (FIG. 12B) of a salivary gland duct implant having a bulb adjacent to the suturing fixture device according to embodiments of the present invention.

DETAILED DESCRIPTION OF THE INVENTION

The present invention will now be described more fully hereinafter with reference to the accompanying drawings, in which embodiments of the invention are shown. This invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The present invention relates to a salivary gland implant device, a kit comprising the implant device, and a method of implanting the device.

Implant Device

The implant device of the invention is used to treat salivary gland disorders including, but not limited to, sialolithisis, salivary gland swelling, kinks, and stones.

In some embodiments, the implant device may be a stent. Upon implantation, the stent may allow saliva to flow postoperatively in the salivary duct along the outer surface of the stent. The stent also may maintain a patent salivary duct.

In certain embodiments, the implant device may be a cannula. Upon implantation, the cannula may allow saliva to flow postoperatively through the salivary duct channel. The cannula may also support the salivary duct after a procedure required to remove stones blocking the salivary duct.

Figure 1A:
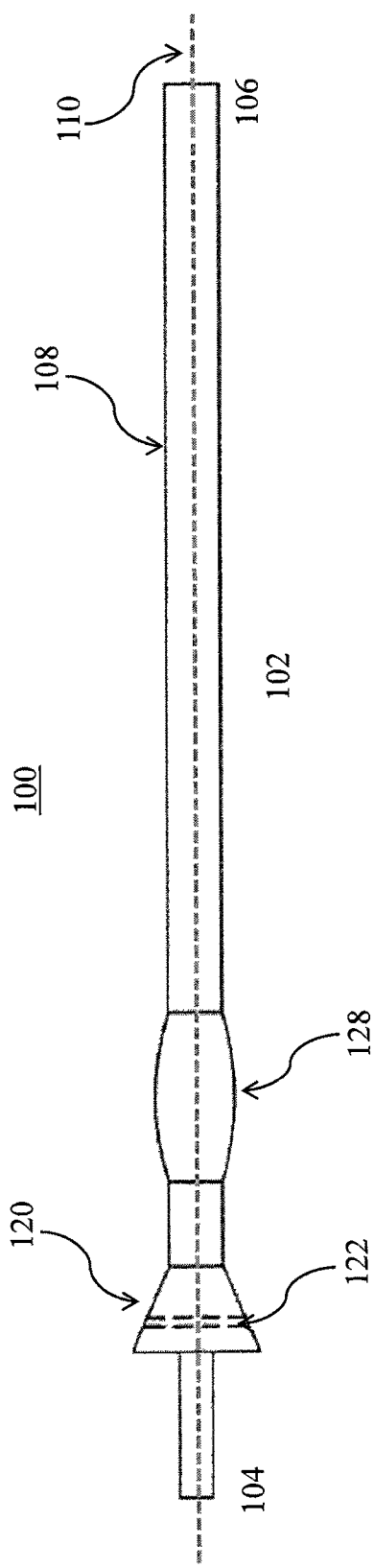
FIGS. 1A and 1B illustrate a side view perspective (FIG. 1A) and an end view perspective (FIG. 1B) of a salivary gland duct implant device according to embodiments of the present invention.
Figure 1B:
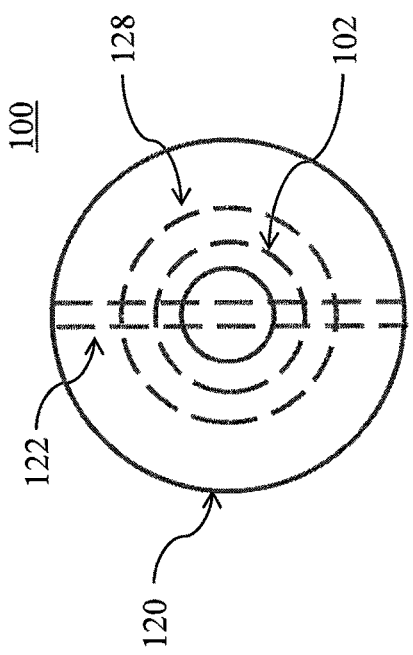

In accordance with certain embodiments, as illustrated in FIG. 1A, an implant device 100 may comprise an elongate body 102 having a proximal end 104 and a distal end 106, an outer surface 108, and an axis 110 that extends through the middle of the elongate body 102 between the proximal end 104 and the distal end 106. In some embodiments, the elongate body 102 may be generally cylindrical in shape and, in certain embodiments, with a substantially uniform circular cross section as shown in FIG. 1B. However, an elliptical or alternative-shaped cross-section may be contemplated based on the physical repair or remedy needed for the particular duct receiving the implant device 100.

In certain embodiments, the elongate body 102 may comprise a rod shape, as illustrated in FIGS. 1A, 1B, 9A, 9B, 11A, and 11B. In such instances, implantation of the device 100 may allow saliva to flow in the salivary duct along the outside of the device 102, and may help maintain a patent salivary duct.

In some embodiments, the elongate body 102 may be tubular and may comprise a lumen 112 (i.e., the bore of the tube-shaped elongate body 102) extending between the proximal end 104 and the distal end 106, as illustrated in FIGS. 2A, 2B, 3A, 3B, 4-7, 8A, 8B, 10A, 10B, 12A, and 12B. The lumen 112 may be used, for example, to allow saliva to flow through the salivary duct, as well as a means to access or inject into a the salivary gland. For instance, the lumen 112 may be used to inject a steroid directly into the salivary gland.

The elongate body 102 may have a length L of about 50 to about 90 mm as shown in FIG. 3A. In certain embodiments, the elongate body 102 may have a length L of about 79 mm to about 110 mm. As illustrated in FIG. 3B, the outer diameter $D_O$ of the elongate body may be about 0.6 to about 2 mm. In embodiments in which the elongate body 102 includes a lumen 112, the elongate body 102 may have an inner diameter $D_I$ in the range of about 0.25 to about 1.5 mm, as long as it is less than the outer diameter $D_O$. In certain embodiments, the outer diameter $D_O$ is about 2 mm and the inner diameter $D_I$ is about 0.5 mm.

The elongate body 102 may be produced from a soft, flexible material such as, but not limited to, silicone rubber, which upon insertion within the salivary duct, provides a requisite degree of comfort for the patient. Alternatively, the implant device's elongate body 102 may be produced from a flexible, but firm, material, such as a thermoplastic elastomer, for example, Pebax®.

In addition, the outer surface 108 and, in embodiments in which the elongate body 102 comprises a lumen 112, inner surface 114 may be coated with Paralyene or any other suitable coating material that facilitates the insertion of the implant device 100 within a duct (not shown), prevents tissue build-up or growth (i.e., non-biointegratable) during the implantation period, and prevents adhesion to the duct walls, thereby allowing for ease of removal and for free flow of saliva in the salivary duct along the outer surface 108.

In some embodiments, the elongate body 102 is radiopaque.

Figure 4:
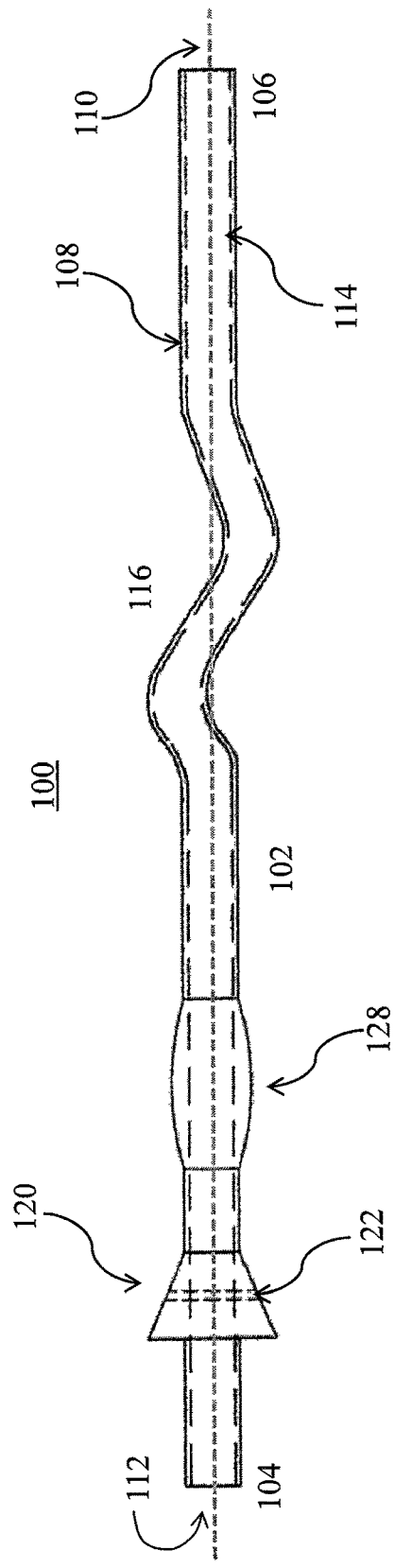
FIG. 4 illustrates a cut-away side view perspective of a salivary gland duct implant device with an anchoring feature according to embodiments of the present invention.
Figure 5:
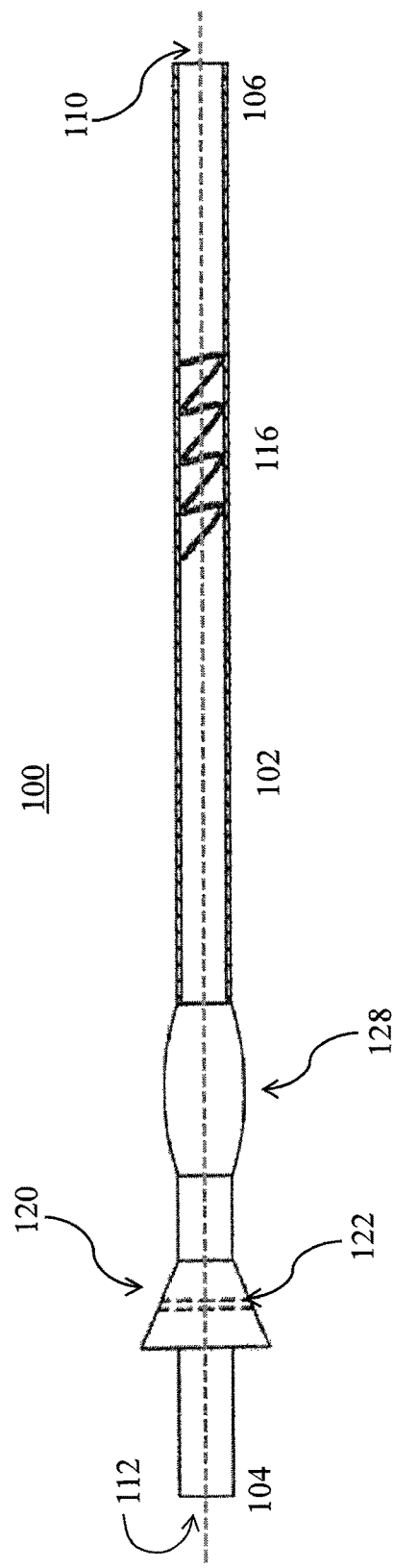
FIG. 5 illustrates a cut-away side view perspective of a salivary gland duct implant device with an anchoring feature according to embodiments of the present invention.
Figure 6:
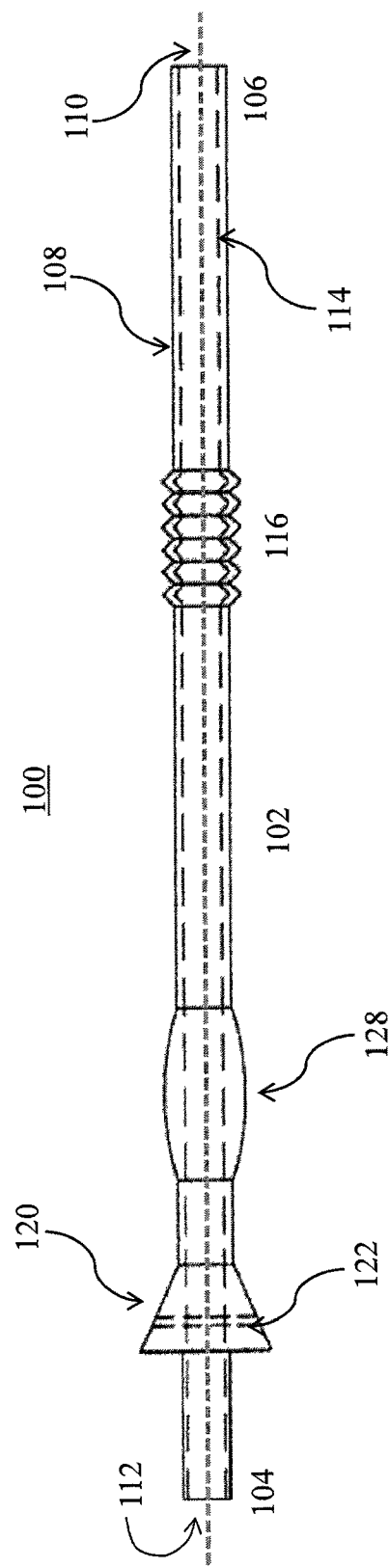
FIG. 6 illustrates a cut-away side view perspective of a salivary gland duct implant device with an anchoring feature according to embodiments of the present invention.

In certain embodiments, the elongate body 102 may include one or more portions comprising an anchoring feature 116 that aid in securing the implant 100 to the salivary gland duct. Examples of such a feature 116 include, but are not limited to, a discontinuity or convoluted shape as illustrated in FIG. 4; a screw shape as illustrated in FIG. 5; and a collapsing/folding spring as illustrated in FIG. 6. In some embodiments, the substantially uniform circular cross section is maintained throughout the portions that comprise the anchoring feature 116.

Figure 7:
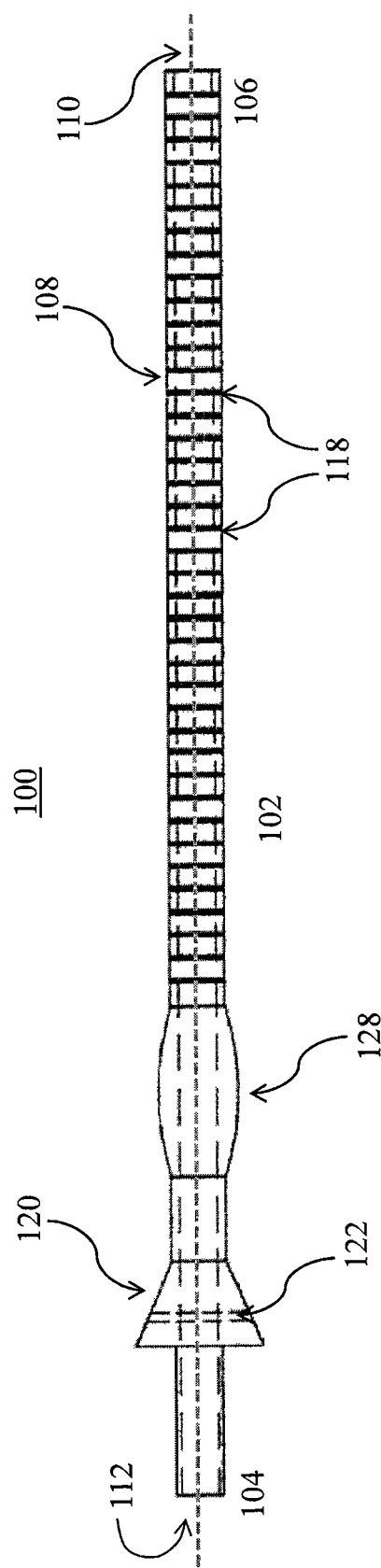
FIG. 7 illustrates a cut-away side view perspective of a salivary gland duct implant device with gradation markings on the outer surface of the implant device according to embodiments of the present invention.

In some embodiments, the elongate body 102 may comprise gradation markings 118 printed onto the outer surface 108, as illustrated in FIG. 7. These gradation markings may allow a physician to accurately determine when the implant device 100 has reached the desired position, particularly when a telescope or the like is not used. To this end, the gradation markings 118 may be, for example, about 0.1 mm to 2 mm apart, or about 1 mm apart.

The elongate body 102 may comprise a suturing fixture 120 offset from the proximal end 104. The suturing fixture 120 may comprise a profile that extends radially outward from the elongate body 102. In embodiments of the invention, the suturing fixture 120 may comprise a cone, such as a truncated cone, in which the axis of the cone is parallel to the axis 110 of the elongate body 102 as shown in FIGS. 1A and 2A. In some embodiments, the axis of the cone coincides with the axis 110 of the elongate body 102. Further, the base of the cone is directed to the proximal end 104 of the elongate body 102.

The suturing fixture 120 may also comprise a disk that extends radially from the axis 110 of the elongate body 102, as illustrated in FIGS. 9A, 9B, 10A, and 10B. The axis of the disc is parallel to the axis 110 of the elongate body 102. In some embodiments, the axis of the disc coincides with the axis 110 of the elongate body.

The suturing fixture 120 may comprise a flexible but firm material, which helps with ease of removal. Such material properties of the suturing fixture 120 allows for the positioning of the implant device 100 in the salivary duct to be discreet and comfortable for the patient.

Figure 8A:
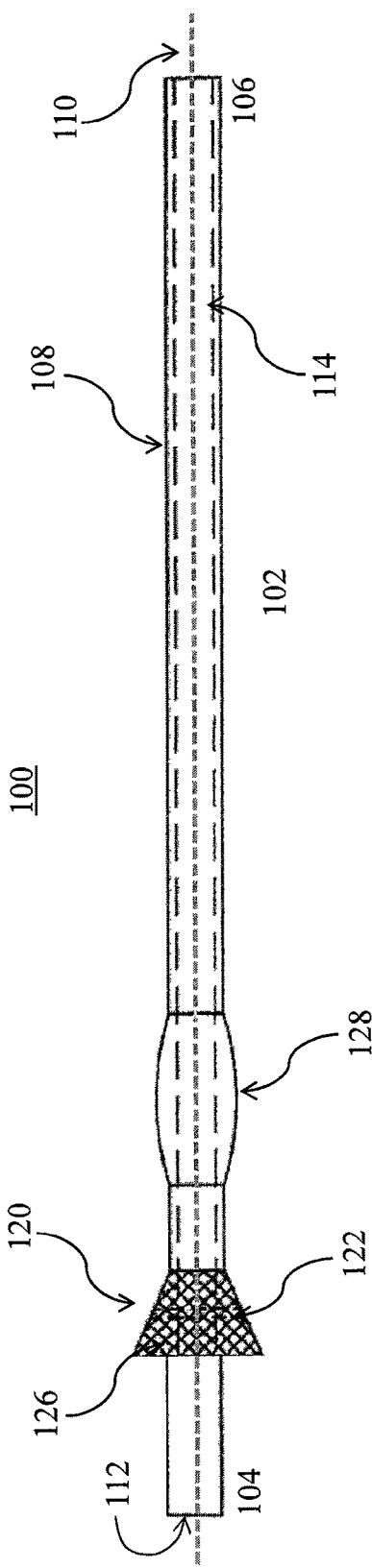
FIGS. 8A and 8B illustrate a cut-away side view perspective (FIG. 8A) and an end view perspective (FIG. 8B) of a salivary gland duct implant device having a suturing fixture with a fiber mesh according to embodiments of the present invention.
Figure 8B:
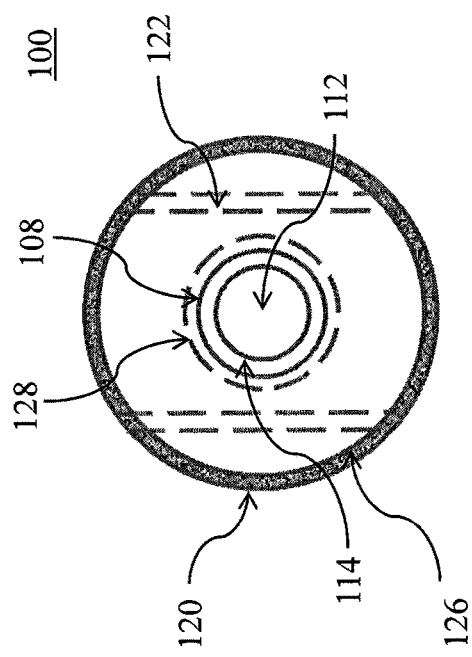
Figure 9A:
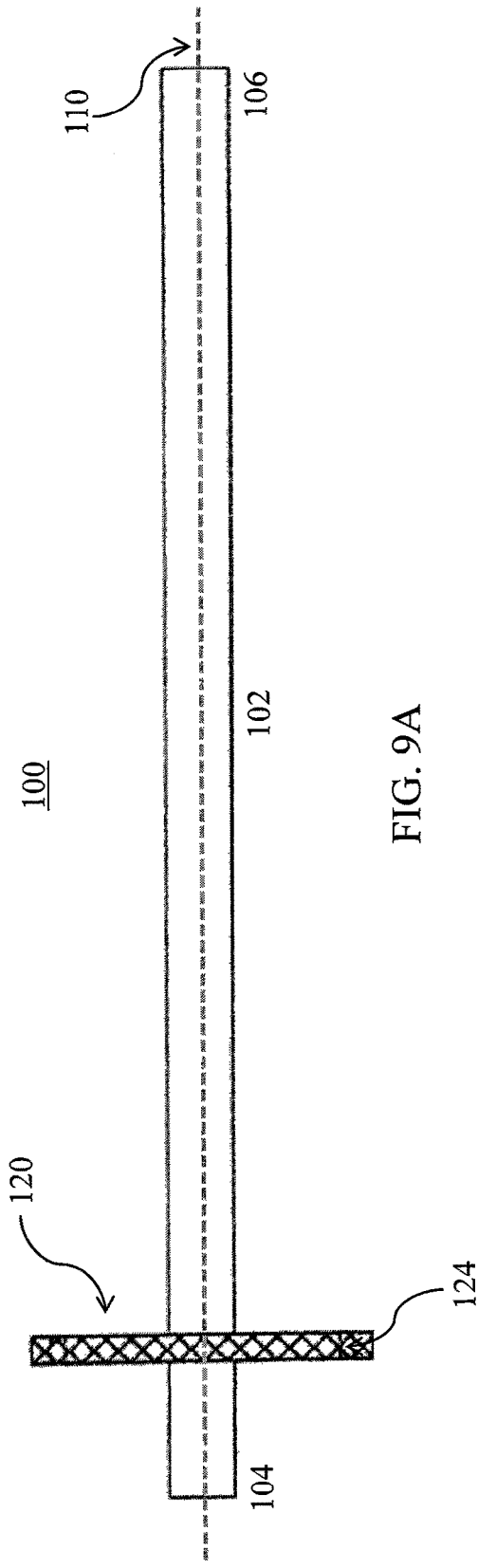
FIGS. 9A and 9B illustrate a side view perspective (FIG. 9A) and an end view perspective (FIG. 9B) of a salivary gland duct implant device having a disk-shaped suturing fixture according to embodiments of the present invention.
Figure 9B:
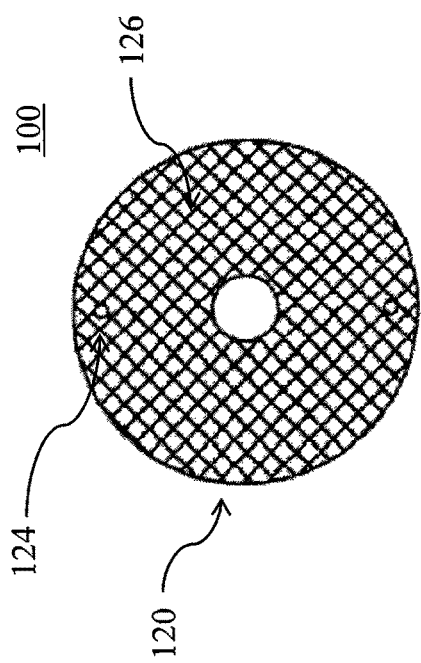
Figure 10A:
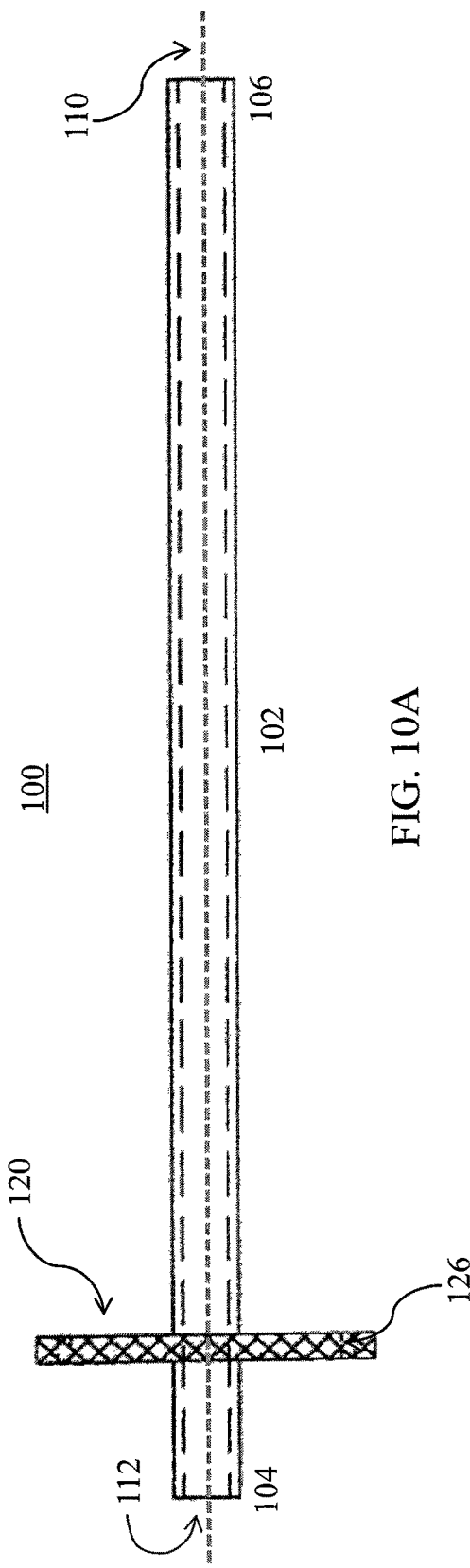
FIGS. 10A and 10B illustrate a cut-away side view perspective (FIG. 10A) and an end view perspective (FIG. 10B) of a salivary gland duct implant device having a disk-shaped suturing fixture according to embodiments of the present invention.
Figure 10B:
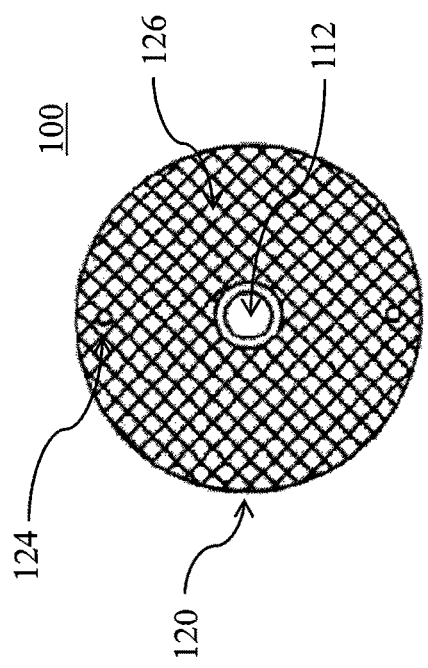
Figure 11A:
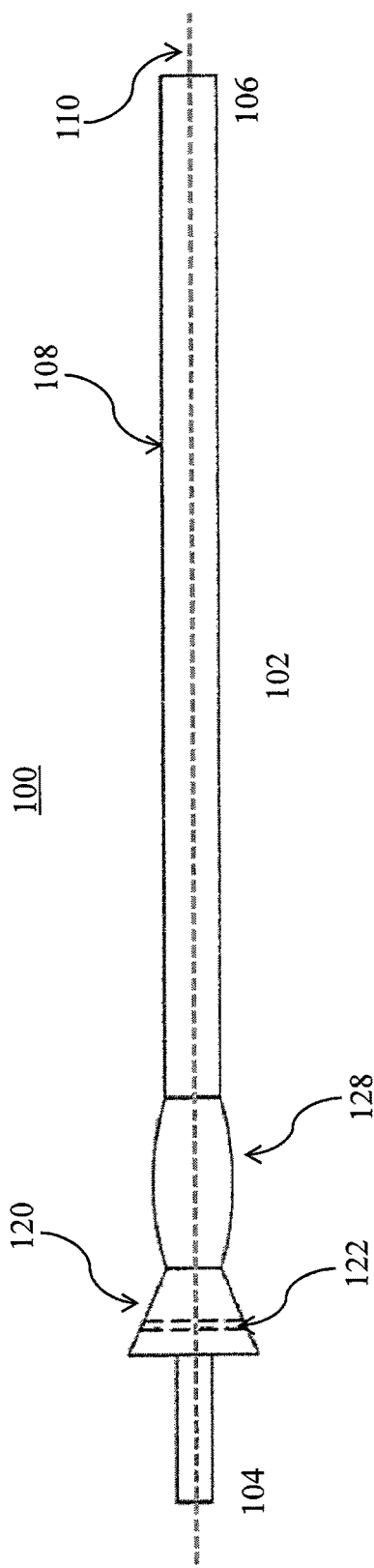
FIGS. 11A and 11B illustrate a side view perspective (FIG. 11A) and an end view perspective (FIG. 11B) of a salivary gland duct implant device having a bulb adjacent to the suturing fixture according to embodiments of the present invention.
Figure 11B:
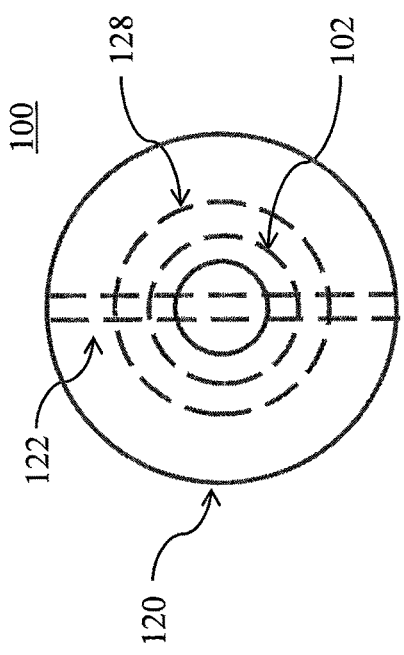

The suturing fixture 120 is used to anchor or secure the implant device 100 to the salivary gland duct. To this end, the suturing fixture 120 may comprise one or more suture channels 122, through which the implant device 100 may be sutured to the salivary gland duct. The number of suture channels 122 and their location may depend on whether the elongate body 102 comprises a lumen 112. For example, when the elongate body 102 comprises a rod-shape, the suturing fixture 120 may comprise one suture channel 122 located, for instance, in the middle of the suturing fixture 120 as shown in FIGS. 1B and 11B. When the elongate body 104 comprises a lumen 112, two suture channels 122 may be present and may be located, as an example, on either side of the lumen 112, as illustrated in FIGS. 2B, 7B, and 8B. Upon implantation, by suturing either side of the lumen 112, the lumen 112 will not be cinched as the sutures are tightened and the implant device 100 is anchored to the salivary gland duct.

The suturing fixture 120 may also comprise one or more suturing holes 124. These suturing holes 124 may be located, for example, on opposite sides of the periphery of the suturing fixture 120 as demonstrated in FIGS. 9B and 10B, or may be distributed in multiple locations along the periphery of the suturing fixture 120 (not shown).

The suturing fixture 120 may comprise a fiber mesh 126 imbedded within the walls of the fixture 120. The fiber mesh 126 prevent the suture from tearing the wall of the fixture 120. The fibers in the mesh 126 may be woven, and may comprise, for example, polyester and/or nylon.

In addition, the implant device 100 may comprise a bulb 128 that contributes in holding the implant device 100 in place. The bulb 128 may also help maintain the integrity of the papilla. The bulb 128 may comprise a radius that is greater than the radius of the elongate body 102, and thereby extends from the surface of the elongate body 102 as shown in FIGS. 1A, 2A, 3A, 6-8, 9A, 10A, 11A, and 12A.

The bulb 128 may be located between the suturing fixture 120 and the distal end 106. In some embodiments, the bulb 128 may be positioned a short distance distal to the suturing fixture 120 as shown in FIGS. 1A, 2A, 3A, 4-8, 9A, and 10A; in this case, the bulb 128 may aid in anchoring the implant device 100, but will not have a direct effect on the papilla. Alternatively, the bulb 128 may be adjacent to the suturing fixture 120 as shown in FIGS. 11A and 12A, and in this position the bulb 128 could support the papilla directly.

In some embodiments, the implant device 100 may comprise an extension (not shown) on the proximal end 104. The length of the extension is about 5 to 10 mm. The extension allows for holding the implant device 100 in place, such as with forceps, while suturing the device in place. Once the device 100 is sutured in place, the extension may be removed, such by being cut off; the removal of the extension allows for a lower profile extending out of the duct and less irritation to the patient.

Scope

The scope of the present invention may comprise a small diameter and is flexible, which is contrast to current sialoendoscopes that are solid. The scope may be used as a means to introduce the implant device into the duct, such as to dilate the duct. The scope may also be used as a measuring tool, such as to determine the depth of an obstruction within the duct. In addition, the scope may be used to aid in irrigating the salivary duct, or as an aid in inserting a balloon catheter. Finally, the scope may be used with other devices including, but not limited to, existing endoscopic devices with which it may serve as a telescope, and a "steering catheter."

Kit

Another aspect of the invention relates to a salivary gland implant device kit comprising the salivary gland implant device. The kit may further comprise a wire guide, and/or a scope, and/or a balloon catheter, and/or a duct dilator.

The wire guide may comprise a coil structure made of materials such as stainless steel. As a result, the wire guide is flexible and can bend as it is inserted into the duct. The wire guide allows the implant device to follow the natural structure of the duct as the device is inserted into the duct. For example, once the wire guide is inserted into the duct, an implant device such as a cannula may be inserted over the guidewire.

The wire guide may have gradations, i.e., lines, printed onto its surface. The gradations may allow a physician to accurately determine when the implant device has reached the desired position upon insertion, without the aid of a telescope.

The scope may be as described above for the present invention.

The balloon catheter and the duct dilator for the kit may include those that are known in the art. The balloon catheter can be used to remove the stone from the salivary duct. The implant device can then be inserted into the duct as a means of maintaining the duct post-procedure.

Method of Implanting the Device

The implant device may be implanted into the salivary gland duct. The method comprises placing the implant device within the salivary gland duct and suturing the suturing fixture of the implant device to a location adjacent the parotid gland. Thus, upon implantation, the distal end may adjacent to the parotid gland and the proximal end may be adjacent to the submandibular gland.

The implant device may be placed within a salivary duct over a predefined period of time (e.g., two to four weeks) in order to restore the physical and/or functional integrity of the duct by, for example, facilitating the flow of saliva. Once the device is implanted within the salivary gland duct, saliva may flow postoperatively in the salivary duct along the outer surface of the implant device, or in some embodiments, through the lumen of the implant device. The device may be placed over the pre-inserted guidewire.

Although embodiments of the present invention and modifications thereof have been described in detail herein, it is to be understood that this invention is not limited to these precise embodiments and modifications, and that other modifications and variations may be effected by one skilled in the art without departing from the spirit and scope of the invention as defined by the appended claims.

What is claimed is:

1. An implant device for placement within a salivary gland duct, the implant device comprising:
   an elongate body having a proximal end and a distal end;
   a suturing fixture offset from the proximal end and the distal end, wherein the suturing fixture comprises the shape of a disk; and
   an outer surface, wherein the suturing fixture comprises a wall and one or more suture channels, wherein the wall comprises a polymer matrix and a fiber mesh imbedded into the matrix and wherein the suture channels extend entirely through the matrix and the mesh of the wall, and wherein upon the placement of the implant device within the salivary gland duct, saliva flows through or along the outer surface of the implant device.

2. The implant device according to claim 1, wherein the elongate body comprises a cylindrical shape.

3. The implant device according to claim 1, wherein the elongate body comprises a lumen between the proximal end and the distal end.

4. The implant device according to claim 1, wherein implant device comprises a stent.

5. The implant device according to claim 1, wherein the implant device comprises a cannula.

6. The implant device according to claim 1, wherein the suturing fixture comprises a profile that extends outward from the elongate body.

7. The implant device according to claim 6, wherein the suturing fixture comprises the shape of a cone.

8. The implant device according to claim 1, wherein the suturing fixture comprises two suture channels.

9. The implant device according to claim 1, wherein the fiber mesh is woven.

10. The implant device according to claim 1, wherein the fiber mesh comprises one of polyester, nylon, and a combination thereof.

11. The implant device according to claim 1, further comprising a bulb on the elongate body.

12. The implant device according to claim 11, wherein the bulb is distally offset from the suturing fixture.

13. The implant device according to claim 11, wherein the bulb is distally adjacent from the suturing fixture.

14. The implant device according to claim 1, further comprising a removable extension on the proximal end.

15. The implant device according to claim 1, wherein the implant device is made from one of a silicone rubber, an elastomeric material, Pebax, and a copolymer.

16. The implant device according to claim 1, wherein the elongate body comprises a coating for facilitating the insertion and removal of the implant device with respect to the salivary duct, and inhibiting biological tissue build up around the implant device.

17. The implant device according to claim 16, wherein the coating comprises a polymer of xylylene.

18. The implant device according to claim 8, wherein the channels are positioned on opposite sides of the elongated body.

19. The implant device according to claim 14, wherein the removeable extension is disposed between the proximal end and the suturing fixture.

20. The implant device of claim 14, wherein the removable extension further comprises a grasping surface.

* * * * *